United States Patent
Chana et al.

(10) Patent No.: US 12,144,533 B2
(45) Date of Patent: Nov. 19, 2024

(54) ELECTROSURGICAL APPARATUS AND METHOD

(71) Applicant: Oxford University Innovation Limited, Oxford (GB)

(72) Inventors: Kamaljit Singh Chana, Oxford (GB); Parvinderpal Singh Sains, Thames Ditton (GB); Vikram Sridhar, Oxford (GB); Richard T. Bryan, Birmingham (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 815 days.

(21) Appl. No.: 17/281,288

(22) PCT Filed: Oct. 2, 2019

(86) PCT No.: PCT/GB2019/052776
§ 371 (c)(1),
(2) Date: Mar. 30, 2021

(87) PCT Pub. No.: WO2020/070491
PCT Pub. Date: Apr. 9, 2020

(65) Prior Publication Data
US 2022/0000535 A1    Jan. 6, 2022

(30) Foreign Application Priority Data

Oct. 3, 2018  (GB) ...................... 1816140

(51) Int. Cl.
*A61B 18/12*    (2006.01)
*A61B 18/00*    (2006.01)
(Continued)

(52) U.S. Cl.
CPC ........ *A61B 18/1206* (2013.01); *A61B 18/082* (2013.01); *A61B 18/10* (2013.01);
(Continued)

(58) Field of Classification Search
CPC .............. A61B 18/1206; A61B 18/082; A61B 18/10; A61B 18/14; A61B 2018/00488;
(Continued)

(56) References Cited

U.S. PATENT DOCUMENTS 6,095,149 A  *  8/2000  Sharkey ............... A61B 18/148
                                                    606/2
7,901,400 B2 *  3/2011  Wham ............... A61B 18/1442
                                                    606/42

(Continued)

FOREIGN PATENT DOCUMENTS

EP    1 862 137 A1   12/2007
EP    2 415 416 A1    2/2012
(Continued)

OTHER PUBLICATIONS

International Search Report and Written Opinion for WO 2020/070491 (PCT/GB2019/052776), dated Dec. 11, 2019, pp. 1-11.
(Continued)

*Primary Examiner* — Linda C Dvorak
*Assistant Examiner* — Abigail Bock
(74) *Attorney, Agent, or Firm* — Thomas|Horstemeyer, LLP

(57) ABSTRACT

Apparatus and methods for electrosurgery are disclosed. In one arrangement, an electrosurgical element and a control system are provided. The electrosurgical element is electrically driven in a first electrical driving mode. The first electrical driving mode is such as to cause heating of human or animal tissue by the electrosurgical element. The heating contributes to modification or cutting of tissue by the
(Continued)

electrosurgical element. The electrosurgical element is electrically driven in a second electrical driving mode. An electrical response of the electrosurgical element is measured during the electrical driving of the electrosurgical element in the second electrical driving mode.

21 Claims, 6 Drawing Sheets

(51) Int. Cl.
    *A61B 18/08*        (2006.01)
    *A61B 18/10*        (2006.01)
    *A61B 18/14*        (2006.01)

(52) U.S. Cl.
    CPC .... *A61B 18/14* (2013.01); *A61B 2018/00488* (2013.01); *A61B 2018/00494* (2013.01); *A61B 2018/00517* (2013.01); *A61B 2018/00601* (2013.01); *A61B 2018/00875* (2013.01); *A61B 2018/1407* (2013.01)

(58) Field of Classification Search
    CPC ........... A61B 2018/00494; A61B 2018/00517; A61B 2018/00601; A61B 2018/00875; A61B 2018/1407
    See application file for complete search history.

(56) References Cited

U.S. PATENT DOCUMENTS

| | | |
|---|---|---|
| 2004/0167508 A1 | 8/2004 | Wham et al. |
| 2006/0052661 A1 | 3/2006 | Gannot et al. |
| 2011/0152857 A1 | 6/2011 | Ingle |
| 2015/0088124 A1* | 3/2015 | Wham ............... A61B 18/1445 606/34 |

FOREIGN PATENT DOCUMENTS

| | | |
|---|---|---|
| EP | 2 823 782 A1 | 1/2015 |
| WO | 2009/124097 A1 | 10/2009 |

OTHER PUBLICATIONS

UK Search Report for GB 1816140.6, dated Mar. 19, 2019, pp. 1-3.
International Preliminary Report on Patentability for WO 2020/070491 (PCT/GB2019/052776), dated Mar. 23, 2021, pp. 1-8.

\* cited by examiner

US 12,144,533 B2

ELECTROSURGICAL APPARATUS AND METHOD

CROSS-REFERENCE TO RELATED APPLICATIONS

This application is the National Stage of International Application No. PCT/GB2019/052776, filed Oct. 2, 2019, which claims priority to GB 1816140.6, filed Oct. 3, 2018, which are entirely incorporated herein by reference.

The present invention relates to electrosurgical apparatus and methods, particularly in the context of performing sub-mucosal endoscopic resection operations and the like.

Sub-mucosal endoscopic resection involves endoscopic removal of abnormal growths in mucosal layers that in most cases have not entered an underlying muscle layer. The procedure can be used, for example, to remove growths from the oesophagus, stomach, colon, or bladder (hollow viscera) and in gynaecological surgery, such as in the cervix or endometrium. It is important in such operations to ensure complete removal of the abnormal growth without excessively removing healthy tissue. One approach for assessing the success of an operation of this type is to test removed matter in a laboratory after the operation. Laboratory testing can determine whether the removal was deep enough by determining whether the muscle layer was reached and/or whether the deepest removed material consists of normal tissue only. Laboratory testing cannot easily be done in real time, so further surgical operations may be needed if the removal was not deep enough, or excessive material may be removed if the removal is too deep.

It is an object of the invention to provide apparatus and methods that allow abnormal growths to be removed more easily and/or more reliably.

According to an aspect of the invention, there is provided an electrosurgical apparatus, comprising: an electrosurgical element; and a control system configured to: electrically drive the electrosurgical element in a first electrical driving mode, the first electrical driving mode being such as to cause heating of human or animal tissue by the electrosurgical element when the apparatus is used in a surgical operation, the heating contributing to modification or cutting of tissue by the electrosurgical element; electrically drive the electrosurgical element in a second electrical driving mode; and measure an electrical response of the electrosurgical element during the electrical driving of the electrosurgical element in the second electrical driving mode, wherein the control system is further configured to use the measured electrical response to determine compositional information about material that is or was in thermal contact with the electrosurgical element during the driving of the electrosurgical element in the second electrical driving mode.

Thus, an apparatus is provided which allows a single electrosurgical element to be used in two distinct modes. In a first electrical driving mode, the electrosurgical element performs the required surgical operations (involving modification or cutting of tissue). In a second electrical driving mode, an electrical response of the electrosurgical element is monitored to sense thermal properties of material in thermal contact with the electrosurgical element. The measurement of thermal properties allows compositional information to be determined, even beneath the surface of the tissue that is directly in contact with the electrosurgical element. The apparatus can thereby provide real time feedback to a surgeon about the nature of tissue adjacent to the electrosurgical element during an operation, without required sophisticated additional equipment to be introduced into the operating area. Where the operation is being performed endoscopically, for example, substantially no changes to endoscopic equipment (catheter assembly, etc.) is needed. The only required difference relative to a single mode approach using an electrosurgical element having the same overall geometrical form would be in the electronics of the control system that allows the electrosurgical element to be driven in the two electrical driving modes.

The inventors have thus recognised that the use of an electrosurgical element that operates by heating tissue electrically can, when electrically driven in a different way, also probe the heat transfer properties of material with minimal or no other modification to the electrosurgical element itself (although some modifications may be made, as described below). As described in detail below, heat transfer properties (e.g. thermal product) are highly sensitive to small changes in composition and can detect even relative subtle changes in tissue. Further, the approach intrinsically samples not only tissue that is in direct contact with the electrosurgical element, but may also sample underlying tissue layers if a heating pulse is long enough. The surgeon can thus effectively see beneath the surface that he is operating on in real time. It is possible, for example, to sense the depth of a muscle layer or other transition between one tissue type and another during a cutting operation, or to verify when a muscle layer or other transition between layers is reached. The apparatus can detect, for example, when a transition between abnormal tissue and normal tissue is achieved, or vice versa, during a cutting operation.

According to an alternative aspect, there is provided an electrosurgical method, comprising: using a electrosurgical element to modify or cut through tissue by driving the electrosurgical element in a first electrical driving mode, the first electrical driving mode being such as to cause heating of the human or animal tissue by the electrosurgical element; electrically driving the electrosurgical element in a second electrical driving mode, and measuring an electrical response of the electrosurgical element during the electrical driving of the electrosurgical element in the second electrical driving mode; and using the measured electrical response to determine compositional information about material that is or was in thermal contact with the electrosurgical element during the driving of the electrosurgical element in the second electrical driving mode.

Embodiments of the invention will now be described, by way of example only, with reference to the accompanying drawings in which corresponding reference symbols indicate corresponding parts, and in which:

FIG. 1 schematically depicts a section through a colon;

FIG. 2 is a schematic side sectional view showing a portion of a side wall of the colon showing different types of abnormal growth;

FIG. 3 schematically depicts an electrosurgical element protruding from a catheter assembly;

Embodiments of the present disclosure involve an electrosurgical element that can obtain information about a surgical site using thermal measurements. Heating (e.g. in the form of a heating pulse) is applied via the electrosurgical element to the surgical site. A response of the electrosurgical element during the heating is analysed to determine heat transfer characteristics of material in thermal contact with the electrosurgical element. The heat transfer characteristics affect how efficiently heat will be conducted away from the electrosurgical element. Heat from the heating pulse penetrates underneath the surface of material directly in contact with the electrosurgical element (typically through several millimetres of material), allowing sub-surface structure to be sensed, such as the relative depth of layers of different composition (e.g. muscle layers). Sensing can be achieved effectively even for relatively low energy pulses, which will typically increase the temperature of tissue being sensed by no more than about two degrees Celsius.

Heat transfer characteristics of materials (e.g. thermal properties such as thermal conductivity, $\kappa$, specific heat capacity, c, and quantities that depend on one or both of these properties) can depend sensitively on the composition (e.g. chemical or structural) of the materials. The thermal product, $\sqrt{\rho c \kappa}$, where $\rho$ is equal to the density, is often a heat transfer characteristic that is particularly sensitive to composition because it takes into account both $\kappa$ and c. Changes in either or both of $\kappa$ and c will typically result in a change in $\sqrt{\rho c \kappa}$. Changes in relative concentrations of different components in a multi-component material can be detected where the different components have different thermal properties. Changes in structure can be detected where there is a density or compositional change.

The inventors have recognised that electrosurgical apparatuses, which are by definition configured to use electrical heating to modify or cut through tissue may be adapted with minimal or no modification to elements that make surgical contact with tissue to performing the above thermal measurements, and that the thermal measurements can provide valuable feedback to a surgeon during operation, particularly where the operation involves removal of material from a multi-layer structure.

One area where embodiments of the present disclosure are particularly advantageous is where abnormal tissue is to be removed from a multi-layer structure such as the oesophagus, stomach, colon, or bladder and/or bladder layers, particularly in the context of an endoscopic operation where space for additional apparatus or modifications at the surgical site and along the path to the surgical site is limited.

Figure 1:
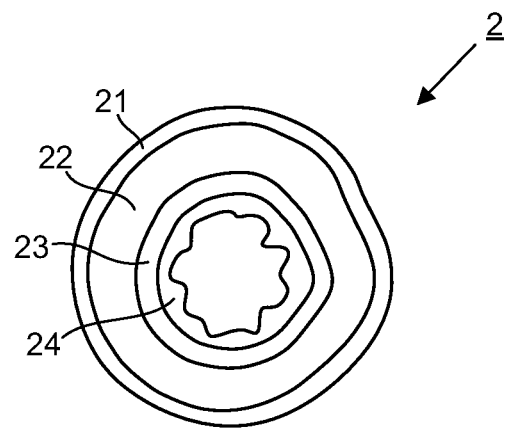

FIG. 1 is a cross-section of colon 2, representing an example multilayer site where an electrosurgical apparatus 10 according to embodiments of the present disclosure may be particularly advantageously applied. The colon 2 comprises a serosa 21, a muscle layer 22, a sub-mucosa 23, and a mucosa 24.

Figure 2:
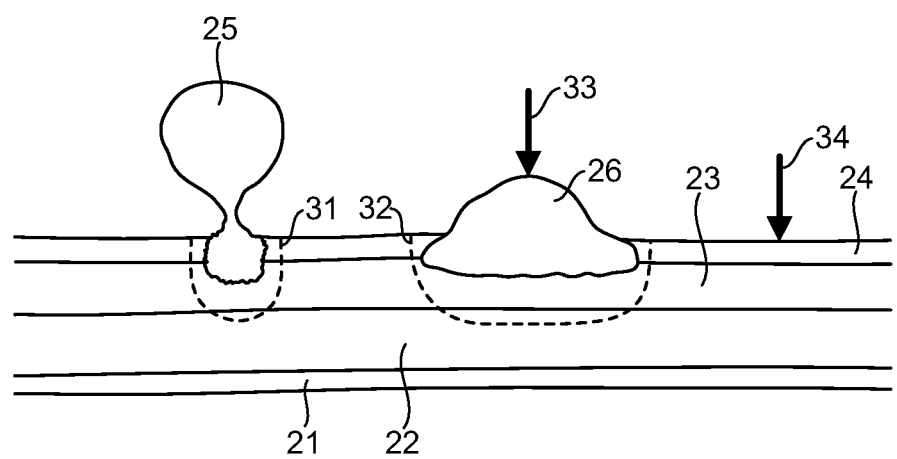

FIG. 2 schematically depicts abnormal growths 25 and 26 (e.g. polyps or tumours) that might occur in such a layered structure. Such growths are often limited to a subset of the layers of the multi-layer structure, such as within either or both of the mucosa 24 and sub-mucosa 23 in this particular example. The growths may take various forms, as indicated schematically by the two examples in FIG. 2. An ideal surgical procedure will completely remove the abnormal growths 25 and 26 with minimal removal of other matter. Example surgical cutting lines are depicted by broken lines 31 and 32. In this example, the cutting lines 31 and 32 extend into a shallow region within the muscle layer 22. By testing for the presence of muscle in material removed by the surgical operation in a laboratory after the operation, it is possible to verify that the cutting operation went as deep as the muscle layer 22. If the cutting operation reaches the muscle layer it is likely that complete removal of the abnormal growth is achieved. It is difficult for a surgeon to ensure that the muscle layer 22 is reached during the operation and/or to avoid taking too much of the muscle layer 22 (i.e. cutting too deeply). Embodiments of the present disclosure assist the surgeon by allowing the surgeon to receive real time feedback about the composition of material adjacent to an electrosurgical element (e.g. a cutting element) at the surgical site.

Figure 3:
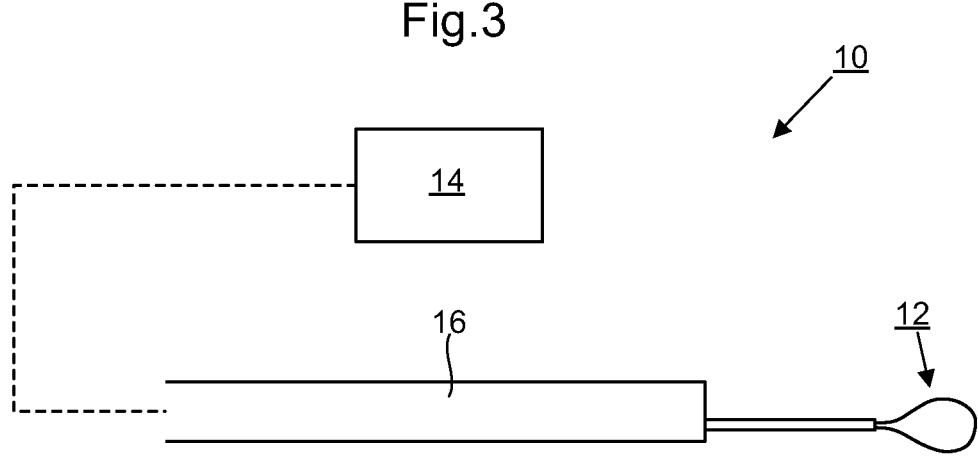

FIG. 3 depicts an electrosurgical apparatus 10 according to an embodiment. The electrosurgical apparatus 10 comprises an electrosurgical element 12 and a control system 14. A catheter assembly 16 allows the electrosurgical element 12 to be delivered to a target site within the human or animal body while maintaining an electrical connection between the electrosurgical element 12 and the control system 14. Catheter systems for such purposes are well known in the art. The catheter assembly 16 may, for example, comprise a longitudinal lumen for the electrosurgical element 12 and associated electrical connections, as well as other lumens to allow other surgical and/or endoscopic equipment to be brought to the surgical site as required.

The control system 14 is configured to electrically drive the electrosurgical element 12 in a first electrical driving mode. The first electrical driving mode is such as to cause heating of human or animal tissue by the electrosurgical element 12 when the apparatus 10 is used in a surgical operation. The heating contributes to (e.g. causes) modification (e.g. coagulation, desiccation, fulguration) or cutting of tissue by the electrosurgical element 12.

Electrosurgical elements for modifying or cutting tissue by heating are known generally in the art and may take various geometries. The electrosurgical element 12 of embodiments of the present disclosure may take any of the forms known in the art, including shapes comprising closed loops, circular loops, elliptical loops, semi-circular loop portions, hooks, needle-shapes, disk shapes, or other shapes. In one particular class of embodiments, the modification or cutting of tissue is part of a sub-mucosal resection operation and measuring an electrical response of the electrosurgical element is used to detect whether the electrosurgical element has penetrated to a muscle layer. Further details on how the electrosurgical element may perform such measurements are provided below.

Figure 4:
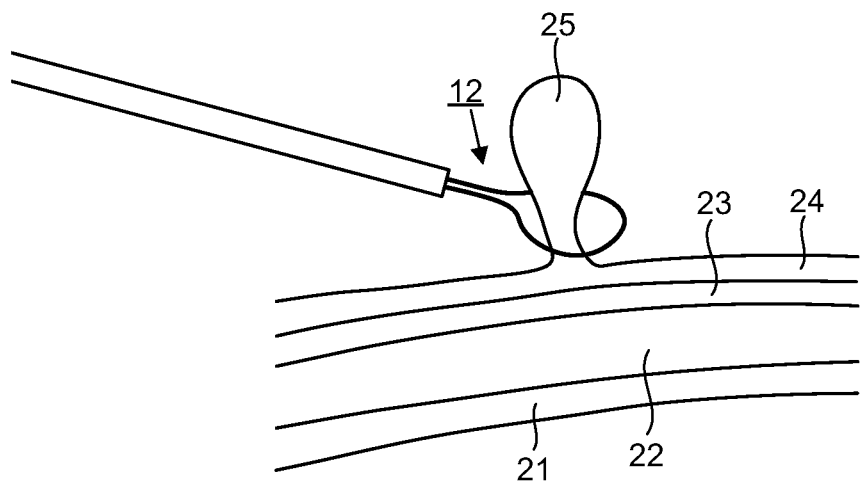
FIG. 4 is a schematic perspective view showing use of an electrosurgical element to remove an abnormal growth.
Figure 5:
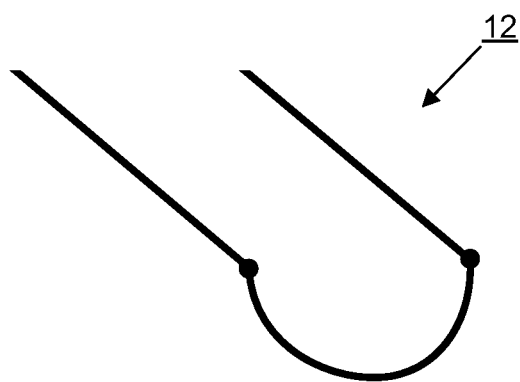
FIG. 5 is a schematic perspective view of an alternative electrosurgical element.

In the example of FIG. 3, the electrosurgical element 12 is provided in the form of a loop. FIG. 4 depicts schematically how the loop may be moved over an abnormal growth 25 prior to cutting into tissue beneath the growth 25 in order to remove the growth, as explained above with reference to FIG. 2. FIG. 5 depicts an alternative semi-circular geometry, which can be used in a similar manner to remove growths by scooping the element underneath the growths.

In an embodiment, the driving of the electrosurgical element 12 in the first electrical driving mode comprises using the electrosurgical element 12 as an active electrode to generate current flow in tissue. In an embodiment, the first electrical driving mode causes intracellular oscillation of ionized molecules by applying a high frequency (e.g. radio frequency) alternating electric field. The oscillation of the ionized molecules causes localized heating of the tissue. The heating contributing to modification or cutting of tissue is predominantly provided by this mechanism in this class of embodiment. The alternating field is focused at the electrosurgical element 12, such that significant heating only occurs in a localized region directly adjacent to the electrosurgical element 12. The electrosurgical element 12 may be configured to operate in a monopolar mode in which current flows from the electrosurgical element 12 to a dispersive electrode placed elsewhere on the patient's body (where the field and current are much more spread out). Alternatively, the electrosurgical element 12 may operate in a bipolar mode in which a further electrode is provided at the surgical site and current flows from the electrosurgical element 12 directly to the further electrode.

In an embodiment, the control system 14 is further configured to electrically drive the electrosurgical element 12 in a second electrical driving mode. In an embodiment, the driving in the second electrical driving mode is such that heat is generated predominantly by resistive heating within the electrosurgical element 12.

Figure 6:
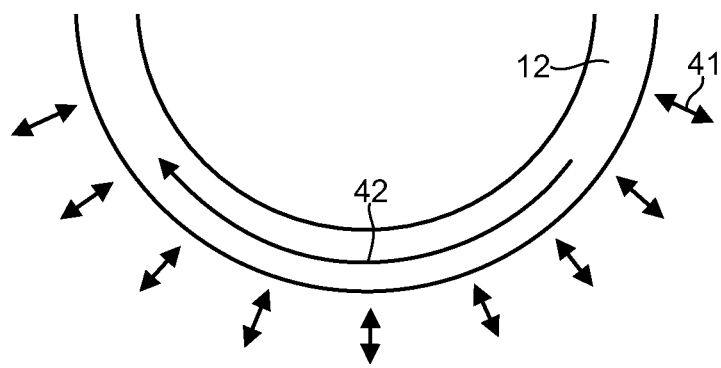
FIG. 6 is a schematic side view of an electrosurgical element with arrows indicating two modes of operation of an electrosurgical element.

FIG. 6 depicts a portion of the electrosurgical element 12 in an embodiment in which the the heating contributing to modification or cutting of tissue during the driving of the electrosurgical element 12 in the first electrical driving mode is generated predominantly by induced intracellular oscillation of ionized molecules in the tissue (with current flow schematically indicated by arrows 41), and the driving in the second electrical driving mode is such that heat is generated predominantly by resistive heating within the electrosurgical element 12 (with current schematically indicated by arrow 42).

While the electrosurgical element 12 is being driven in the second electrical driving mode, the control system 14 measures an electrical response of the electrosurgical element 12. The electrical response (e.g. a change in resistance dependent on the temperature of the electrosurgical element 12) depends on heat transfer characteristics of tissue in thermal contact with the electrosurgical element 12. The response can therefore be used to determine compositional information about tissue in close proximity to the electrosurgical element 12. In an embodiment, the control system 14 applies a heating pulse via the electrosurgical element 20 and measures a response of the electrosurgical element 12 to the heating pulse. The control system 12 may thus comprise a power supply, or be connectable to a power supply, and data processing hardware to control the supply of the heating power and to control the measurement process. The control system 12 may be connected to mains power or be powered by a battery. The control system 12 may comprise a memory for storing measurements and/or calibration data for analysing measurements. Example electronics for inclusion in the control system 14 are described below with reference to FIG. 12.

In an embodiment, the heating pulse is applied by driving an electrical current through a portion of the electrosurgical element 12 to create resistive heating (Joule heating). In an embodiment, the control system 14 applies a plurality of the heating pulses. Each heating pulse is applied by driving an electrical current through the electrosurgical element 12. In an embodiment, top hat shaped pulses are applied, but other pulse shapes could be used if desired. In an embodiment, the plurality of heating pulses each have the same duration. The heating pulses are regularly spaced apart from each other (i.e. the spacing between each pair of heating pulses is the same). The duration of each heating pulse is equal to or less than the separation between the heating pulses. This provides time for the electrosurgical element 12 to cool between each heating pulse. In an embodiment, the separation between heating pulses is the same as the duration of each heating pulse. This provides a minimum time for the electrosurgical element 12 to cool between heating pulses, thereby allowing a high measurement sampling rate and, as a consequence, high accuracy (by averaging) and/or time resolution.

The control system 14 measures an electrical response of the electrosurgical element 12 to the heating pulses, for example by measuring a voltage dependent on the resistance of a portion of the electrosurgical element 12 through which the current flows and the size of the current. The resistance varies as a function of the temperature of the electrosurgical element 12. Measuring the electrical response thus corresponds to measuring a temperature response of the electrosurgical element 12.

The electrical response of the electrosurgical element 12 to the heating pulses can be used to determine compositional (e.g. chemical and/or structural) information about materials adjacent to the electrosurgical element 12 because the variation in the temperature of the electrosurgical element with time will depend on the heat transfer characteristics of those materials.

In an embodiment, a response to the heating pulse is compared with the response to a corresponding heating pulse applied to a reference material. The size of the response, the variation of the response as a function of time, or various other aspects of the response may be considered. Any deviation from the response measured for the reference material may be used to detect a deviation from the reference material (e.g. indicating that the material being sensed is of a different type to the reference material, for example a different tissue type). The nature of the heating pulses may be selected to achieve optimum sensitivity for the particular region being measured. This may involve selecting particular pulse shapes, amplitudes, durations and/or repetition rates, for example. In the example of FIG. 6, the heating of the first electrical driving mode comprises generation of current within the tissue and the heating of the second electrical driving mode is resistive (Joule heating) within the electrosurgical element.

Figure 7:
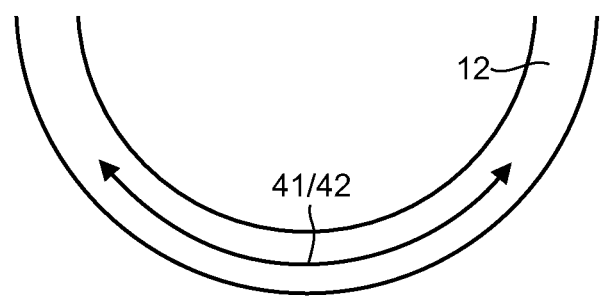
FIG. 7 is a schematic side view of an electrosurgical element with an arrow indicating an alternative two modes of operation of an electrosurgical element.

In other embodiments, the heating for both of the first and second electrical driving modes is predominantly via Joule heating within the electrosurgical element 12. In an embodiment, the electrical current follows the same path through the electrosurgical element during the resistive heating in both of the first and second electrical driving modes, as depicted schematically in FIG. 7. This approach can be implemented particularly efficiently because the same conductive structure is used for producing both types of heating. A high level of resistive heating can be used to modify or cut tissue while a lower level heating can be used to sense compositional information (without modifying the structure of tissue in contact with the electrosurgical element 12, which could undermine the accuracy of the measurement of compositional information).

Figure 8:
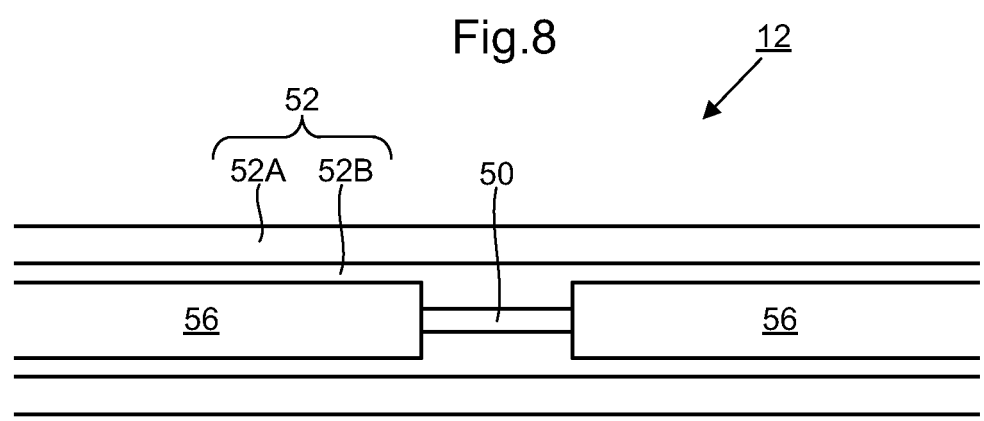
FIG. 8 is a radially inward view onto an alternative electrosurgical element in which a resistive element is mounted on a support structure.

In an embodiment, an example of which is depicted in FIG. 8, the electrosurgical element 12 comprises a resistive element 50 mounted on a solid support structure 52. In an embodiment, the support structure 52 is a multi-layered structure. In an embodiment, the support structure 52 comprises an electrically insulating layer 52B (e.g. a thin film layer) and an electrically conductive base portion 52A. The electrically conductive base portion 52A may define the overall form of the electrosurgical element 12 and thereby take any of the forms discussed above for the electrosurgical element (e.g. loop etc.). In the example of FIG. 8, the electrically conductive base portion 52A has a loop shape and FIG. 8 is a view radially inwards onto a radially outer surface of the electrically conductive base portion 52A. The electrically insulating layer 52B may cover only a portion of the electrically conductive base portion 52A so as to allow another portion of the electrically conductive base portion 52A to be in direct electrical contact with tissue. The electrically insulating layer 52B is positioned between the resistive element 50 and the electrically conductive base portion 52A to prevent shorting of the resistive element 50 by the electrically conductive base portion 52A. In an embodiment, the resistive element 50 is mounted on the support structure 52 in such a way that at least 10% of the surface area of the resistive element 50 is in contact with the support structure 52, optionally more than 30%, optionally around 50%. In an embodiment the resistive element 50 is a thin film resistive element (e.g. thin film resistance thermometer). In an embodiment the resistive element 50 comprises a thin film of platinum or gold. In an embodiment, the resistive element 50 has a first surface configured to face towards the region to be sensed (facing out of the page in FIG. 8) and a second surface facing towards the support structure 52 (facing into the page in FIG. 8). It is understood that the first and second surfaces are the large surfaces of the thin film (and do not include any of the very thin side surfaces). In an embodiment no portion of the entity being sensed is present between the second surface and the support structure 52. In the particular example of FIG. 8, substantially 50% of the surface of the resistive element 50 is in contact with the support structure 52. In the example shown, electrically conductive tracks 56 are formed on the electrically insulating layer 52B to provide the required electrical connections to the resistive element 50. The presence of the support structure 52 allows relatively large currents to be applied to the resistive element 50 without the resistive element 50 overheating, which could damage the resistive element 50 and/or tissue that is in contact with the resistive element 50.

In various embodiments the resistive element 50 is metallic. In these embodiments, the resistive element 50 may be configured such that the thermal contact between the resistive element 50 and the tissue being sensed will not result in a significant reduction in the electrical resistance between one end of the resistive element 50 and the other end of the resistive element 50. This may be achieved by arranging for the resistivity of the resistive element 50 to be much lower than the resistivity of the tissue to be sensed or by positioning a thin layer of electrically insulating material between the resistive element 50 and the tissue to be sensed.

In an embodiment, the heating contributing to the modification or cutting of tissue during the driving of the electrosurgical element 12 in the first electrical driving mode is generated predominantly by resistive heating in the support structure 52. The resistive heating may occur in an electrically conductive base portion 52A, for example. In such an embodiment, the electrical driving of the electrosurgical element 12 in the second electrical driving mode predominantly involves current flow through the resistive element 50 to generate resistive heating in the resistive element 50. Thus, a single common support structure 52 provides mechanical support for two resistive elements performing separate operations: the electrically conductive base portion 52A in which resistive heating is applied to perform surgical operations; and the resistive element 50 in which resistive heating is used to measure thermal properties and therefore composition of tissue adjacent to the electrosurgical element 12. For example, the electrically conductive base portion 52A can be made thick enough to support the relatively high levels of heating and mechanical stresses imposed by the surgical operations, while the resistive element 50 can be provided in thin film form suitable for providing highly sensitive measurements of thermal properties.

In an embodiment, the electrosurgical element 12 comprises an elongate metallic element (e.g. a length of wire) and the path of the electrical current is predominantly longitudinally along the elongate metallic element (i.e. parallel to a longitudinal axis of the elongate metallic element) in both of the first and second electrical driving modes. Alternatively, the electrical current may follow a first path through the electrosurgical element 12 during the resistive heating in the first electrical driving mode (e.g. longitudinally along an elongate metallic element) and follow a second path through the electrosurgical element 12 during the resistive heating in the second electrical driving mode (e.g. through a resistive element mounted on the elongate metallic element). The first path is different from the second path. The arrangement of FIG. 8 is an example of such an embodiment. The first path may be electrically insulated from the second path (e.g. using an electrically insulating layer 52B such as that described above with reference to FIG. 8).

The peak heating power delivered during the driving of the electrosurgical element 12 in the first electrical driving mode will typically be significantly higher than the peak heating power delivered during the driving of the electrosurgical element 12 in the second electrical driving mode, optionally more than twice as high, optionally more than 5 times as high, optionally more than 10 times as high, optionally more than 25 times as high, optionally more than 50 times as high, optionally more than 100 times as high. To avoid interference between the heating for implementing the surgical operation (generated during driving in the first electrical driving mode) and the measurement of the electrical response of the electrosurgical element 12 during the driving in the second electrical driving mode, the control system 14 may be configured to drive the electrosurgical element 12 in the first electrical driving mode at a different time to driving the electrosurgical element in the second electrical driving mode. The first and second electrical driving modes may occur during non-overlapping time windows for example. A gap between the first and second electrical driving modes may be long enough to allow tissue to cool completely after the heating of the first electrical driving mode.

As described above, in embodiments of the disclosure the control system 14 determines compositional information about material in thermal contact with the electrosurgical element 12 during driving in a second electrical driving mode, by using a measured electrical response of the electrosurgical element 12 to the driving. In some embodiments, the compositional information comprises a variation in composition as a function of distance from the electrosurgical element 12. This is possible because heat generated by the electrosurgical element 12 propagates some distance away from the electrosurgical element 12 and the electrical response of the electrosurgical element 12 to the heating will be affected by the heat transfer characteristics of all portions of material that are reached to a significant extent by the heating. Where plural layers of different composition are in thermal contact with the electrosurgical element 12, two or more of these layers can be sampled by the heating if the layers are in sufficiently good thermal contact with the electrosurgical element. Portions of material that are closer to the electrosurgical element 12 will contribute to the measured electrical response of the electrosurgical element 12 sooner after the start of the heating than portions of material that are further away. It is therefore possible to analyse the measured electrical response to distinguish between contributions from different portions of material, for example different layers of material in the multilayer structure. In an embodiment, the control system 14 analyses the measured electrical response of the electrosurgical element 12 to identify one or more target time periods, each target time period being defined as a time period in which the electrical response of the electrosurgical element 12 is determined predominantly by a different combination of one or more of the plural layers. For example, in a case where the electrosurgical element 12 is brought into contact with tissue at point 33 in FIG. 2, up to four different target time periods could be identified (depending on the level of heating and pulse duration, which would both need to be high enough to allow the heating pulse to penetrate significantly through all the layers during the driving of the electrosurgical element 12 in the second electrical driving mode): a first target time period in which only tissue in the abnormal growth 26 contributes; 2) a second target time period in which only the tissue in the abnormal growth 26 and the underlying sub-mucosa 23 contribute; 3) a third target time period in which only the tissue in the abnormal growth 26, the sub-mucosa 23, and the muscle layer 22 contribute; and 4) a fourth time period in which the tissue in the abnormal growth 26, the sub-mucosa 23, the muscle layer 22, and the serosa 21 contribute. In the case where the electrosurgical element 12 is brought into contact with tissue at point 34 in FIG. 2, a different four target time periods could potentially be identified: a first target time period in which only the mucosa 24 contributes; 2) a second target time period in which only the mucosa 24 and the sub-mucosa 23 contribute; 3) a third target time period in which only the mucosa 24, the sub-mucosa 23, and the muscle layer 22 contribute; and 4) a fourth time period in which the mucosa 24, the sub-mucosa 23, the muscle layer 22, and the serosa 21 contribute. The same principle applies in other situations where plural layers are provided.

Figure 9:
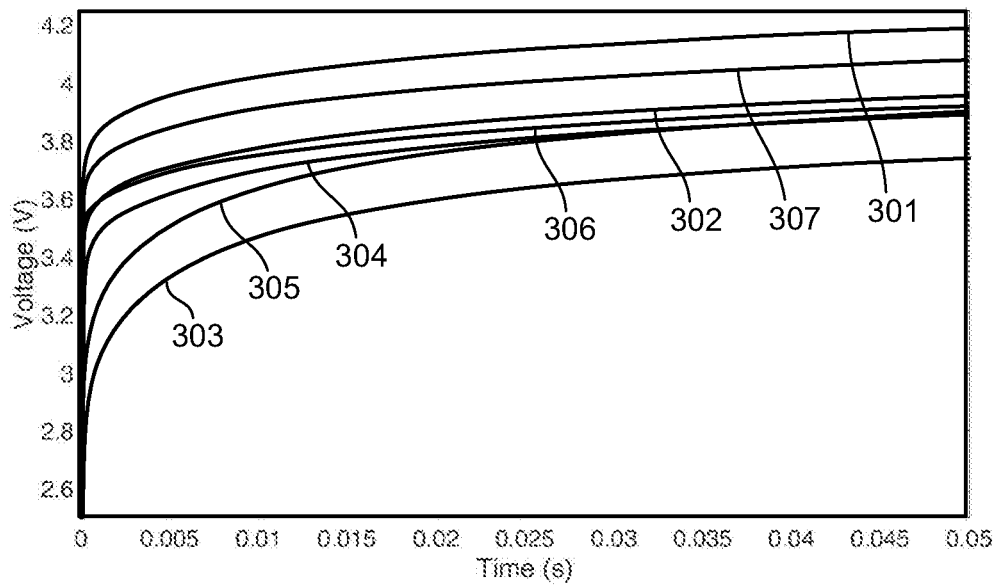
FIG. 9 is a graph showing changes of resistance with time during heating of a resistive element in contact with different layers of a sample of porcine belly.

Use of a resistive element to detect different types of tissue by electrically driving the resistive element and measuring the electrical response of the resistive element to detect differences in heat transfer characteristics of tissue was tested by performing the measurement with the resistive element in contact with different layers of dead porcine tissue (a piece of pork belly) at 17.5 degrees C. Results were obtained in near real time and were reproducible. Example data is depicted in FIG. 9, which shows a variation of a measured voltage across the resistive element with time during a heating pulse. Differences in thermal product between different types of tissue leads to characteristic differences in the behaviour of the measured voltage against time, demonstrating that the approach can distinguish sensitively between different types of tissue. The different curves are marked as follows: skin (301); fat (302); muscle (303); fascia (304); deep muscle (305); deep fat (306); and bone (307).

Figure 10:
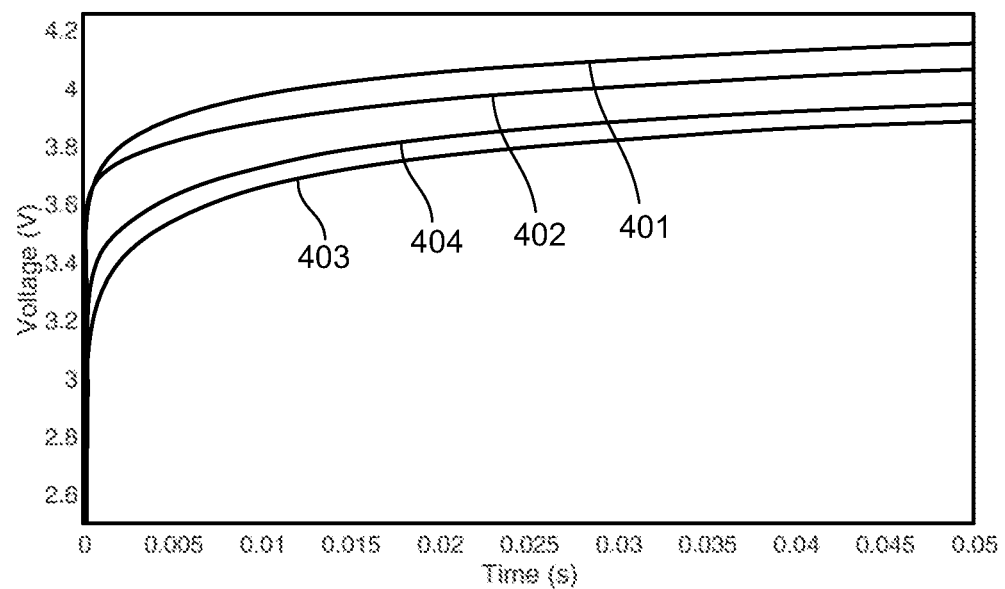
FIG. 10 is a graph showing changes of resistance with time during heating of a resistive element in contact with different layers of a sample of porcine thigh.

FIG. 10 depicts corresponding data for a case where the resistive element was brought into contact with different layers of porcine thigh tissue at 17.5 degrees C. The different curves are marked as follows: skin (401); fat (402); muscle (403) and fascia (404).

Figure 11:
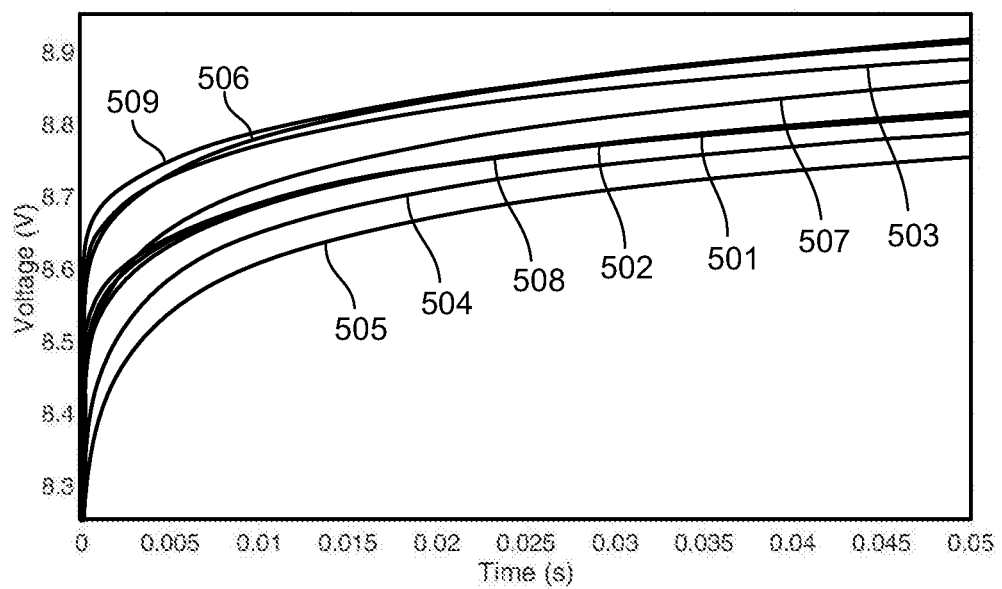
FIG. 11 is a graph showing changes of resistance with time during heating of a resistive element in contact with different porcine organs.

FIG. 11 depicts data obtained from experiments involving using the resistive element to measure different porcine organs. The data demonstrates further that the approach is sensitive to different tissue types. The different curves are marked as follows: liver at 11.2 degrees C. (501); heart at 9 degrees C. (502); lungs at 13.5 degrees C. (503); aorta at 11.2 degrees C. (504); oesophagus at 13.5 degrees C. (505); larynx at 11 degrees C. (506); trachea at 11.7 degrees C. (507); thyroid at 13.7 degrees C. (508); and pleura at 11 degrees C. (509).

The experiments providing the data of FIG. 9-11 were all performed on dead tissue. Differences in thermal product between different tissue types are even larger for living tissue due to the presence of different reaction products/concentrations due to differences in metabolism. Metabolism in cancer cells, for example, is often very different to the metabolism of surrounding cells, leading to markedly different levels of $CO_2$ for example.

Figure 12:
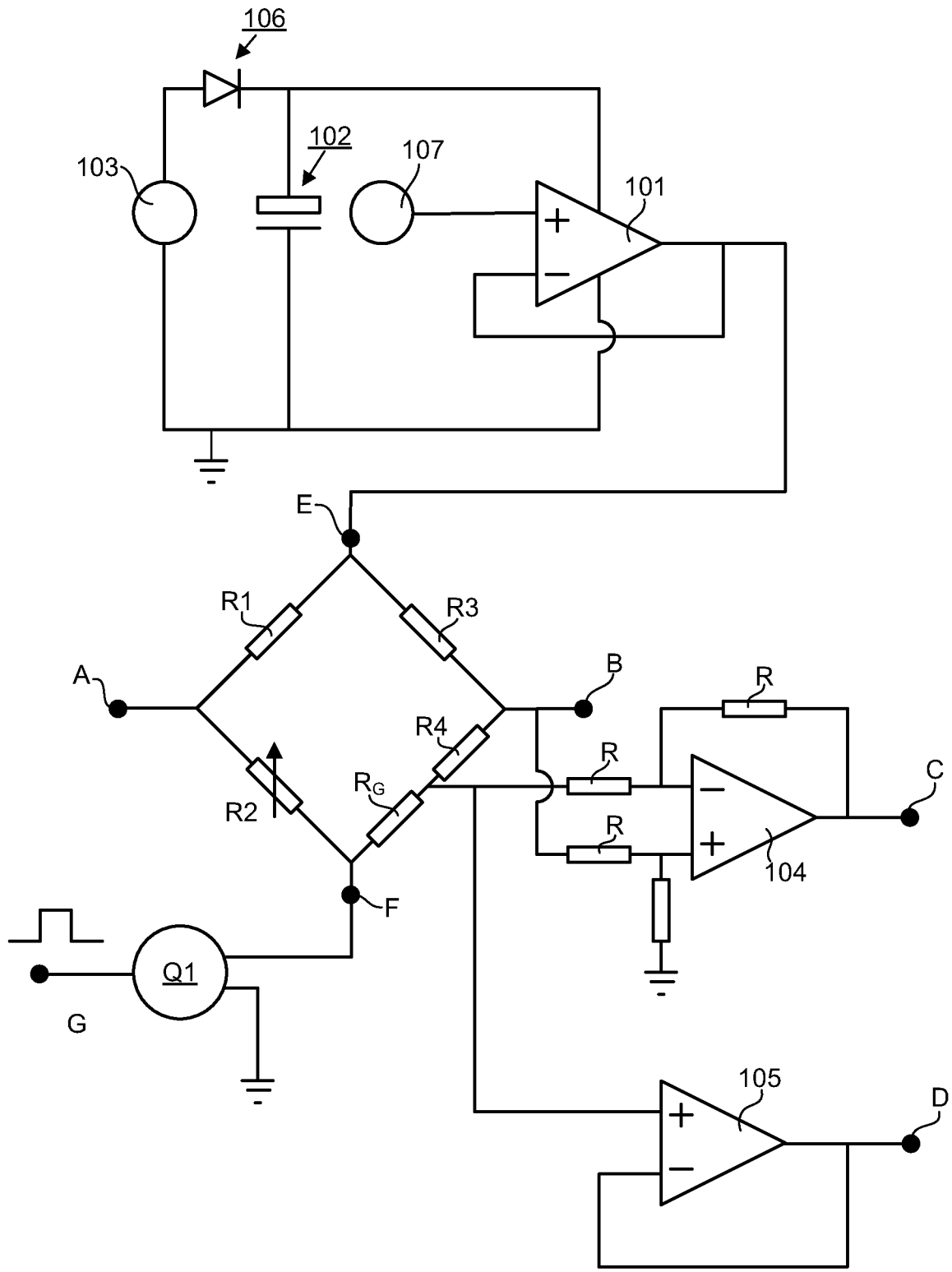
FIG. 12 depicts example circuitry for measuring a response of a sensor element to heating pulses.

FIG. 12 depicts example circuitry for use in the control system 14 for measuring the response of the electrosurgical element 12 to heating pulses. The following elements are shown in FIG. 12:
  101 Power amplifier (e.g. about 10 A RATED)
  102 Charge store (e.g. about 40,000 µF)
  103 Power supply (e.g. about 30V DC)
  104 Differential amplifier for I
  105 Buffer amplifier for V
  R1+R2 Bridge balance
  R3+$R_G$ Active bridge half
  Q1 Power switch (e.g. fast, low resistance MOSFET)
  C Output of current I
  D Output of voltage V
  E High side of bridge
  F Low side of bridge
  G Signal pulse control
  R4 Current sense shunt (resistance) (e.g. 20 mΩ)
  A+B Diagnostic differential signal outputs for development
  106 Diode rectifier
  107 Voltage reference A voltage generated by voltage supply 103 is fed through a rectifier diode 106 to charge a high capacity storage 102. The storage 102 provides a high current power source to the power amplifier 101. A voltage reference 107 sets a high side voltage presented at E.

A bridge is created between the points A, E, B and F. In an example, R3 and $R_G$ are about 1.0 Ohms, and R1 and R2 are about 470 Ohms. A power switch device Q1 is provided to rapidly bring point F to ground under a signal pulse at G. The circuit enables a steady bridge voltage to be maintained without demanding a high gain bandwidth from the power amplifier 101. The power amplifier 101 needs only to maintain a DC level. High energy pulses of precise timing are made possible using a fast MOSFET power switch for Q1 at the low side of the bridge.

When the bridge is energised the differential voltage points (A & B) will provide a voltage corresponding to the Ohmic resistance change of the gauge element $R_G$ (e.g. the portion of the electrosurgical element 12 being measured, for example a resistive element 50). The other resistors in the bridge are chosen to have a very low parts-per-million (ppm)

change in resistance with temperature. Therefore observed bridge voltages are only a function of the gauge $R_G$.

For precise measurements of heat transfer to the electrosurgical element, and from the electrosurgical element to material in contact with the electrosurgical element, it is desirable to measure the voltage V and current I across the portion of the electrosurgical element being measured. The current is determined from the output of the circuit at C. The voltage is determined from the output of the circuit at D. Thus the energy input and the corresponding rise in temperature can be determined and the heat transfer function to the material in contact with the electrosurgical element can be computed.

The total energy and energy rate can be controlled by varying the reference voltage 107 and the pulse duration at G.

The circuit allows a modest power source to store energy to deliver very high energy density pulses. Electronic controls may be provided to activate the power level and pulses duration whilst reading the voltage signals at C and D. The electronic controls may be provided by the measurement system 8 or processing unit 18, or both.

In an embodiment, fast ADC to storage in computer memory is employed leaving time to compute the heat transfer data from which quantitative measurements can be performed and compared to calibrated lookup tables to provide qualitative assessments of the composition of the region being sensed.

The invention claimed is:

1. An electrosurgical apparatus, comprising:
an electrosurgical element; and
a control system configured to:
  electrically drive the electrosurgical element in a first electrical driving mode, the first electrical driving mode being such as to cause heating of human or animal tissue by the electrosurgical element when the apparatus is used in a surgical operation, the heating contributing to modification or cutting of tissue by the electrosurgical element;
  electrically drive the electrosurgical element in a second electrical driving mode; and
  measure an electrical response of the electrosurgical element during the electrical driving of the electrosurgical element in the second electrical driving mode, wherein the control system is further configured to use the measured electrical response to determine compositional information about material that is or was in thermal contact with the electrosurgical element during the driving of the electrosurgical element in the second electrical driving mode, wherein:
  the electrical driving of the electrosurgical element in the second driving mode is such as to generate heating predominantly by resistive heating within a resistive element of the electrosurgical element and the measuring of the electrical response of the electrosurgical element during the electrical driving of the electrosurgical element in the second electrical driving mode comprises measuring an electrical response of the resistive element to the heating generated within the resistive element.

2. The apparatus of claim 1, wherein the control system is configured to drive the electrosurgical element in the first electrical driving mode at a different time to driving the electrosurgical element in the second electrical driving mode.

3. The apparatus of claim 1, wherein the compositional information comprises a variation in composition as a function of distance from the electrosurgical element.

4. The apparatus of claim 1, wherein:
the electrosurgical element is such that heat generated in the electrosurgical element during the driving of the electrosurgical element in the second electrical driving mode can propagate through plural layers of different composition when such plural layers are in thermal contact with the electrosurgical element; and
the control system is configured to analyse the measured electrical response of the electrosurgical element to identify one or more target time periods, each target time period being defined as a time period in which the electrical response of the electrosurgical element is determined predominantly by a different combination of one or more of the plural layers.

5. The apparatus of claim 1, wherein the control system is configured to determine the compositional information by comparing a measured electrical response of the electrosurgical element during the driving of the electrosurgical element in the second electrical driving mode to a stored reference response.

6. The apparatus of claim 1, wherein the heating contributing to modification or cutting of tissue during the driving of the electrosurgical element in the first electrical driving mode is predominantly caused by generating electrical currents in the tissue.

7. The apparatus of claim 1, further comprising a catheter assembly for delivering the electrosurgical element to a target site within the human or animal body while maintaining an electrical connection between the electrosurgical element and the control system.

8. The apparatus of claim 1, wherein the electrosurgical element comprises a resistive element mounted on a solid support structure.

9. The apparatus of claim 8, wherein:
the heating contributing to the modification or cutting of tissue during the driving of the electrosurgical element in the first electrical driving mode is generated predominantly by resistive heating in the support structure; and
the electrical driving of the electrosurgical element in the second electrical driving mode predominantly involves current flow through the resistive element to generate resistive heating in the resistive element.

10. The apparatus of claim 8, wherein the resistive element is mounted on the support structure in such a way that at least 10% of the surface area of the resistive element is in contact with the support structure.

11. The apparatus of claim 10, wherein the resistive element is a thin film resistive element having a first surface facing away from the support structure and a second surface facing towards the support structure.

12. The apparatus of claim 1, wherein a peak heating power delivered during the driving of the electrosurgical element in the first electrical driving mode is higher than a peak heating power delivered during the driving of the electrosurgical element in the second electrical driving mode.

13. The apparatus of claim 12, wherein the peak heating power delivered during the driving of the electrosurgical element in the first electrical driving mode is at least ten times higher than the peak heating power delivered during the driving of the electrosurgical element in the second electrical driving mode.

14. The apparatus of claim 1, wherein the heating contributing to modification or cutting of tissue during the driving of the electrosurgical element in the first electrical driving mode is generated predominantly by resistive heating within the electrosurgical element.

15. The apparatus of claim 14, wherein the electrical current follows the same path through the electrosurgical element during the resistive heating in both of the first and second electrical driving modes.

16. The apparatus of claim 15, wherein the electrosurgical element comprises an elongate metallic element and the path of the electrical current is predominantly longitudinally along the elongate metallic element in both of the first and second electrical driving modes.

17. The apparatus of claim 14, wherein the electrical current follows a first path through the electrosurgical element during the resistive heating in the first electrical driving mode and follows a second path through the electrosurgical element during the resistive heating in the second electrical driving mode, the first path being different from the second path.

18. The apparatus of claim 17, wherein the first path is electrically insulated from the second path.

19. An electrosurgical method, comprising:
using a electrosurgical element to modify or cut through tissue by driving the electrosurgical element in a first electrical driving mode, the first electrical driving mode being such as to cause heating of the human or animal tissue by the electrosurgical element;
electrically driving the electrosurgical element in a second electrical driving mode, and measuring an electrical response of the electrosurgical element during the electrical driving of the electrosurgical element in the second electrical driving mode; and
using the measured electrical response to determine compositional information about material that is or was in thermal contact with the electrosurgical element during the driving of the electrosurgical element in the second electrical driving mode, wherein:
the electrical driving of the electrosurgical element in the second driving mode is such as to generate heating predominantly by resistive heating within a resistive element of the electrosurgical element and the measuring of the electrical response of the electrosurgical element during the electrical driving of the electrosurgical element in the second electrical driving mode comprises measuring an electrical response of the resistive element to the heating generated within the resistive element.

20. The method of claim 19, wherein the modification or cutting of tissue is part of a sub-mucosal resection operation and the measuring of the electrical response of the electrosurgical element is used to detect whether the electrosurgical element has penetrated to a muscle layer.

21. An electrosurgical apparatus, comprising:
an electrosurgical element; and
a control system configured to:
electrically drive the electrosurgical element in a first electrical driving mode, the first electrical driving mode being such as to cause heating of human or animal tissue by the electrosurgical element when the apparatus is used in a surgical operation, the heating contributing to modification or cutting of tissue by the electrosurgical element;
electrically drive the electrosurgical element in a second electrical driving mode; and
measure an electrical response of the electrosurgical element during the electrical driving of the electrosurgical element in the second electrical driving mode, wherein the control system is further configured to use the measured electrical response to determine compositional information about material that is or was in thermal contact with the electrosurgical element during the driving of the electrosurgical element in the second electrical driving mode, wherein:
the electrosurgical element is such that heat generated in the electrosurgical element during the driving of the electrosurgical element in the second electrical driving mode can propagate through plural layers of different composition when such plural layers are in thermal contact with the electrosurgical element; and
the control system is configured to analyse the measured electrical response of the electrosurgical element to identify one or more target time periods, each target time period being defined as a time period in which the electrical response of the electrosurgical element is determined predominantly by a different combination of one or more of the plural layers.

* * * * *